(12) United States Patent
Constantz

(10) Patent No.: US 7,906,152 B2
(45) Date of Patent: Mar. 15, 2011

(54) METHODS AND DEVICES FOR THE IN SITU DISSOLUTION OF RENAL CALCULI

(75) Inventor: Brent R. Constantz, Menlo Park, CA (US)

(73) Assignee: Cordis Corporation, Bridgewater, NJ (US)

( * ) Notice: Subject to any disclaimer, the term of this patent is extended or adjusted under 35 U.S.C. 154(b) by 89 days.

(21) Appl. No.: 11/295,716

(22) Filed: Dec. 5, 2005

(65) Prior Publication Data

US 2006/0233891 A1    Oct. 19, 2006

Related U.S. Application Data

(63) Continuation of application No. 11/048,638, filed on Jan. 31, 2005, now abandoned, which is a continuation of application No. 10/105,804, filed on Mar. 20, 2002, now Pat. No. 6,866,651.

(51) Int. Cl.
*A61K 33/18* (2006.01)
*A01M 37/00* (2006.01)
*A61B 17/221* (2006.01)
*A61M 25/00* (2006.01)
*A01N 59/00* (2006.01)
*A01M 31/00* (2006.01)

(52) U.S. Cl. ............... 424/666; 604/93.01; 604/508; 604/509; 606/127; 606/198; 606/200

(58) Field of Classification Search .......... 424/666; 514/891, 968
See application file for complete search history.

(56) References Cited

U.S. PATENT DOCUMENTS

| 4,156,721 | A | | 5/1979 | Gustowski et al. |
|---|---|---|---|---|
| 4,295,464 | A | | 10/1981 | Shihata |
| 4,349,029 | A | | 9/1982 | Mott |
| 4,474,180 | A | | 10/1984 | Angulo |
| 4,763,652 | A | | 8/1988 | Brisson et al. |
| 4,781,677 | A | | 11/1988 | Wilcox |
| 4,790,812 | A | | 12/1988 | Hawkins, Jr. et al. |
| 4,794,928 | A | | 1/1989 | Kletschka |
| 4,807,626 | A | | 2/1989 | McGirr |
| 4,808,153 | A | | 2/1989 | Parisi |
| 4,825,851 | A | | 5/1989 | Cocks et al. |
| 4,845,125 | A | | 7/1989 | Geier |
| 4,892,089 | A | | 1/1990 | Cocks et al. |
| 4,984,575 | A | | 1/1991 | Uchiyama et al. |
| 4,997,435 | A | * | 3/1991 | Demeter .................. 606/127 |
| 5,060,650 | A | | 10/1991 | Wurster et al. |
| 5,065,741 | A | | 11/1991 | Uchiyama et al. |
| 5,065,761 | A | | 11/1991 | Pell |
| 5,275,605 | A | | 1/1994 | Winkler |
| 5,328,471 | A | | 7/1994 | Slepian |
| 5,403,324 | A | | 4/1995 | Ciervo et al. |
| 5,460,610 | A | * | 10/1995 | Don Michael ........ 604/101.03 |
| 5,496,330 | A | | 3/1996 | Bates et al. |
| 5,845,125 | A | | 12/1998 | Nishimura et al. |

OTHER PUBLICATIONS

MedlinePlus medical encyclopedia: kidney stones [online] retrieved from the Internet Jan. 4, 2007 http://www.nlm.nih.gov/medlineplus/ency/article/000458.htm Sep. 13, 2005 pp. 1-4.*
Bryant (The Practice of Surgery 1876, vol. II, second edition London, p. 80).*
Oosterlinck, W., et al., "Chemolysis of Calcium Containing Urinary Calculi. A Review," (1994) *Acta Urologica Belgica*, 62(2):31-37.
Pfister, Richard C., et al., "Percutaneous Chemolysis of Renal Calculi," (1994) *Urologic Radiology*, 6(2):138-143.

* cited by examiner

*Primary Examiner* — Ernst V Arnold

(57) ABSTRACT

Methods and devices for at least reducing the mass of, if not dissolving, renal calculi in situ are provided. In the subject methods, a renal calculus is contacted, e.g. flushed, with an acidic dissolution solution in situ, where the acidic dissolution solution is a solution of a strong, inorganic acid, e.g. hydrochloric acid. In many embodiments, the renal calculus is first enclosed in an isolated local environment of a device prior contact with the dissolution solution. Also provided are novel devices and kits for practicing the subject invention.

1 Claim, 4 Drawing Sheets

METHODS AND DEVICES FOR THE IN SITU DISSOLUTION OF RENAL CALCULI

TECHNICAL FIELD

The field of this invention is nephrolithiasis and the treatment thereof.

BACKGROUND OF THE INVENTION

Nephrolithiasis, also known as urolithiasis or urinary tract stone disease, is the term used to refer to the condition in which renal calculi or kidney stones occupy one or more locations in the urinary tract, e.g. major calices, minor calices, renal pelvis, ureter, etc. Renal calculi or kidney stones spontaneously develop in the ureter and can cause significant health problems, including pain, bleeding, blockage of the ureter, etc.

A number of different types of kidney stones can form in the urinary tract. Approximately 75 to 85% of all stones are calcium stones, which are typically made up of calcium oxalate and/or calcium phosphate, where the calcium phosphate is typically hydroxyapatite or brushite. Uric acid stone are stones made up of crystallized uric acid and account for approximately 5 to 8% of all observed kidney stones. Cystine stones are rare, accounting for about 1% of all observed stones. Finally, struvite stones ($MgNH_4PO_4$) account for approximately 10 to 15% of all observed stones and are typically associated with the presence of a bacterial infection.

While a significant portion of stones will spontaneously pass out of the body and may even be asymptomatic, treatment is indicated in a large number of cases. As such, a variety of different treatment protocols have been developed. Representative treatment protocols include: dietary changes, pharmacological intervention, and surgical intervention.

Surgical intervention is typically reserved for situations where the stone(s): (a) does not pass after a reasonable period of time and causes constant pain; (b) is too large to pass on its own; (c) blocks the urine flow; (d) causes ongoing urinary tract infection; (e) damages the kidney tissue or causes constant bleeding; or (e) has grown larger (as seen on follow up x-ray studies). A variety of different surgical procedures have been developed, including minimally invasive procedures such as: extracorporeal shockwave lithotripsy (ESWL); percutaneous nephrolithotomy; and ureteroscopic stone removal.

Another minimally invasive procedure that has found some use is chemolysis, in which the urinary tract is irrigated with a stone solvent, such as an organic acid solution. Chemolytic procedures provide some advantages over other treatment protocols, as the stone can be completely dissolved and removed, smaller stones can be removed along with larger ones, and stones that are difficult to access can be treated. However, known chemolytic procedures do not work effectively on all types of stones and require long treatment periods, with the patient finding the treatment protocol tedious and uncomfortable.

As such, there is continued interest in the development of new chemolytic procedures for use in the treatment of disease conditions characterized by the presence or renal calculi, where of particular interest would be the development of a protocol in which calcium containing stones, particularly calcium oxalate and calcium phosphate containing stones, are rapidly dissolved.

Relevant Literature

Patents of interest include U.S. Pat. Nos. 5,845,125 and 5,275,605. Also of interest are U.S. Pat. Nos. 4,295,464; 4,474,180; 4,790,812; 4,807,626; 4,825,851; 5,403,324; and 5,496,330. Literature references of interest include: Pfister & Dretler, Urol. Radiol. (1984) 6:138-143 and Oosterlink & Verbeeck, Acta Urologica Belgica (1994) 62:31-37.

SUMMARY OF THE INVENTION

Methods and devices are provided for at least reducing the mass of the renal calculi in situ. In the subject methods, a renal calculus is contacted, usually flushed, with an acidic dissolution solution of a strong inorganic acid. In certain embodiments, a device is employed to enclose the renal calculus in an isolated local environment, and the local environment is flushed with the dissolution solution. The subject methods find use in the treatment of disease conditions characterized by the presence of renal calculi, e.g. nephrolithiasis and related conditions.

DESCRIPTION OF THE SPECIFIC EMBODIMENTS

Figure 1:
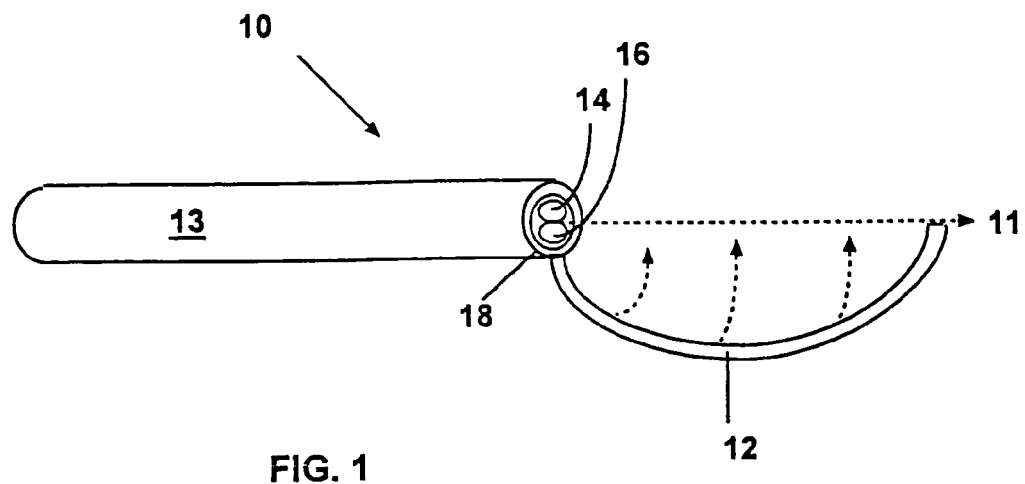
FIG. 1 provides a first cross-sectional view of a dissolution device according to the subject invention.

Methods and devices are provided for use in at least reducing the mass of renal calculi in situ. In the subject methods, renal calculi are contacted, usually flushed, with an acidic dissolution solution of a strong, inorganic acid. In certain embodiments, the renal calculi are enclosed in an isolated local environment using a dissolution device, and the local environment is flushed with the solution. Also provided by the subject invention are novel dissolution devices for practicing the subject methods. The subject invention finds use in a variety of applications, including the treatment of disease conditions characterized by the presence of renal calculi, e.g. nephrolithiasis.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It must be noted that, as used in this specification and the appended claims, the singular forms "a," "an" and "the" include plural reference unless the context clearly dictates otherwise. Unless defined otherwise all technical and scientific terms used herein have the same meaning as commonly understood to one of ordinary skill in the art to which this invention belongs.

Where a range of values is provided, it is understood that each intervening value, to the tenth of the unit of the lower limit, unless the context clearly dictates otherwise, between the upper and lower limit of that range and any other stated or intervening value in that stated range, is encompassed within the invention. The upper and lower limits of these smaller ranges may independently be included in the smaller ranges, and such embodiments are also encompassed within the invention, subject to any specifically excluded limit in the stated range. Where the stated range includes one or both of the limits, ranges excluding either or both of those included limits are also included in the invention.

All publications mentioned herein are incorporated herein by reference for the purpose of describing and disclosing components that are described in the publications that might be used in connection with the presently described invention.

Methods

As summarized above, the invention provides a method for at least reducing the mass of, and in some cases completely dissolving, a renal calculus in situ. By in situ is meant that the calculus at least reduced in mass in a location of the urinary tract of a host, where urinary tract includes the minor calices, major calices, renal pelvis, ureter, bladder and urethra. Thus, the subject methods provide a means for at least reducing the mass of a renal calculus in vivo, where the renal calculus is present in one of the minor calices, major calices, renal pelvis, ureter, bladder and urethra of the host being treated.

Nature of Target Renal Calculi

As summarized above, the subject invention provides a method for at least reducing the mass of a renal calculus by contacting the renal calculus in situ with an acidic dissolution solution, as described in greater detail infra. As such, the subject methods are particularly suited for use in the dissolution of renal calculi that are soluble in acidic environments.

One type of renal calculus which can be dissolved according to the subject invention is a calcium comprising calculus, i.e. a calculus that is made up of a calcium containing compound, such as calcium oxalate, calcium phosphate, e.g. hydroxyapatite, carbonated hydroxyapatite, and the like. The stones may further include additional components, such as struvite, e.g. $MgNH_4PO_4$. As such, the subject methods are suitable for the dissolution of calcium stones and struvite stones.

Contact with an Acidic Dissolution Solution

As mentioned above, the target calculus is contacted with an acidic dissolution solution in situ under conditions sufficient to at least reduce the size or mass of the target renal calculi. Specifically, the target calculus is contacted with an acidic dissolution solution under conditions such that the pH of the local environment of the renal calculus is maintained at a subphysiological level for a sufficient period of time for the desired amount of demineralization of the target calculus to occur. Typically, the pH is maintained at a value that does not exceed about 5 and usually does not exceed about 4, and more usually does not exceed about 3. In many embodiments, the pH of the local environment ranges from between 0 and 1. Within the above range, the pH may be constant or variable over the course of the demineralization procedure, i.e. over the period of time during which the pH of the local environment is maintained at a subphysiological value.

The time period during which the local pH is maintained at a subphysiological level in the local environment of the target calculus is sufficient for the desired amount of mass reduction, e.g. demineralization, to occur. As such, the pH of the local environment is maintained at a subphysiological value in the local environment for a period of time ranging from about 5 to 200 minutes, usually from about 5 to 100 minutes and more usually from about 5 to 30 minutes.

The pH of the local environment may be maintained at a subphysiological level using any convenient protocol. Of particular interest in many embodiments is the use of a dissolution solution that is introduced into the local environment of the target calculus and is capable of locally increasing the proton concentration in the local environment of the target calculus. By capable of locally increasing the proton concentration is meant that the dissolution solution, upon introduction into the local environment of the target calculus, as described in greater detail below, is capable of increasing the hydrogen ion concentration or $[H^+]$ in the local environment of the target calculus. In other words, the solution is capable of reducing the pH in the local environment of the target calculus to the requisite subphysiologic level for the required mass reduction or demineralization to occur.

Dissolution Solutions

A feature of many embodiments of the subject invention is the use of an acidic dissolution solution in which the solution comprises a strong, inorganic acid. The acidic dissolution or treatment solution will generally have a pH of less than about 6.5, where the pH is usually less than about 4.0 and more usually less than about 3.0. In many preferred embodiments, the pH ranges from 0 to 2, and usually 0 to 1. Strong inorganic acids of interest are: hydrochloric, hydrobromic, hydroiodic, sulfuric, nitric, etc. The acid can be a concentrated acid, or can be diluted. Upon dilution, the concentration of the strong inorganic acid will generally be from about 10 N to about 0.01 N, preferably between 5.0 N to 0.1 N.

In many embodiments of the subject invention, the acid solution is hypertonic, by which is meant that the osmolarity of the solution is greater than that of a red blood cell, i.e. the osmolarity is greater than 300 mosmol. The solution may be rendered hypertonic by including any convenient component or components in the solution which provide for the desired elevated osmolarity.

Any convenient agent that is capable of increasing the osmolarity of the solution may be employed, where suitable agents include salts, sugars, and the like. In many embodiments, the agent that is employed to render the solution hypertonic is one or more, usually no more than three, and more usually no more than two, different salts. Generally, the salt concentration in these embodiments of the solution is at least about 100 mosmol, usually at least about 200 mosmol and more usually at least about 300 mosmol, where the concentration may be as high as 3000 mosmol or higher, depending on the particular salt being employed to render the solution hypertonic, where the solution may be saturated with respect to the salt in certain embodiments. Salts that may be present in the subject solutions include: NaCl, $MgCl_2$, Ringers, etc. where NaCl is preferred in many embodiments.

Of particular interest in many embodiments is the use of hydrogen chloride solutions. Hydrogen chloride solutions finding use in the subject methods have an HCl concentration that is sufficient to provide for the requisite pH in the local environment of the target calculus. Generally, the concentration of HCl in the solution ranges from about 0.001 to 1.0 N, usually from about 0.01 to 1.0 N and more usually from about 0.1 to 1.0 N. In many embodiments, the hydrogen chloride solution will further include one or more salts which make the solution hypertonic, as described above. In certain preferred embodiments, the salt is NaCl, where the concentration of NaCl in the solution is at least 0.05 M, usually at least 0.10 M, and more usually at least 0.15 M, where the concentration may be as high as 0.25 M or higher. In certain embodiments, the solution will be saturated with NaCl.

Reducing the pH of the Local Environment

As mentioned above, in the subject methods the dissolution solution is introduced into the local environment in which the target calculus is present in a manner sufficient to maintain the pH of the local environment at the requisite subphysiological level for a sufficient period of time for the desired amount of mass reduction or demineralization to occur. As such, the subject methods generally involve contacting the target calculus with the dissolution solution. The manner in which contact is achieved may be static or dynamic. By static is meant that a predetermined amount of dissolution solution is introduced into the local environment of the calculus and maintained in the local environment of the calculus for the entire treatment period, without the addition of further quantities of dissolution solution. By dynamic is meant that the dissolution solution is introduced into the local environment of the target calculus one or more times, including continuously, during the treatment period.

During the dissolution procedure, protons from the local environment are removed as a result of the demineralization process. As such, it is often desirable to introduce the dissolution solution into the local environment of the target calculus in a dynamic manner. Dynamic introduction of the dissolution solution typically involves flushing the local environment with the dissolution solution, where flushing involves a continuous flow of the dissolution solution over one or more, usually all of, the surfaces of the target calculus, where the flow may be under pressure (e.g. where the fluid is emitted from the delivery device under enhanced pressure, as described in greater detail infra). In other words, the dissolution fluid is continuously flowed through the local environment of the calculus for the period of time required for the desired amount of demineralization and mass reduction to occur. In many embodiments, fluid is simultaneously removed from the local environment of the calculus such that the overall volume of fluid in the local environment of the calculus remains substantially constant, where any difference in volume at any two given times during the treatment period does not exceed about 50%, and usually does not exceed about 10%. In this manner, the pressure of the localized environment of the calculus is maintained at a substantially constant value, thereby minimizing traumatic impact on the vessel walls at the site of the target calculus.

Where the target calculus is flushed with the dissolution solution, the flow rate of the dissolution solution through the local environment of the calculus is generally at least about 1 volume/minute, usually at least about 2 volumes/minute and more usually at least about 10 volumes/minute, where the flow rate may be as great as 100 volumes/minute or greater, but usually does not exceed about 1000 volumes/minute and more usually does not exceed about 500 volumes/minute, where by "volume" is meant the volume of the local environment of the target calculus.

When treatment involves dynamic flushing of the local environment of the target calculus, the total amount of dissolution fluid that is passed through the local environment that includes the target calculus during the treatment period typically ranges from about 0.5 to 50 liters, usually from about 0.5 to 5.0 liters and more usually from about 0.5 to 2.0 liters. In contrast, where a static methodology is employed, the total amount of dissolution fluid that is introduced into the local environment of the calculus ranges from about 100 ml to 1 liter, and usually from about 100 to 500 ml.

Nature of Local Environment

The local environment in which the pH is maintained at a subphysiologic value during the subject methods may vary. In certain embodiments, the local environment is the entire urinary tract or a portion thereof, in which the natural walls of the urinary tract or portion thereof make up at least a portion of the boundary of the local environment. For example, in those embodiments where the target calculus is contacted with the dissolution solution by irrigating the urinary tract with the dissolution solution, the entire urinary tract will make up the local environment in which a subphysiologic pH is maintained.

In other embodiments where only a portion of the urinary tract makes up the local environment, a device that isolates a portion of the urinary tract from the remainder of the urinary tract may be one that blocks a passageway, e.g. with a balloon. For example, the device may comprise a balloon which blocks the opening of the ureter into the renal pelvis, thereby producing an isolated local environment bounded by the walls of the renal pelvis, the major and minor calices and the balloon.

In many preferred embodiments, a device is employed that comprises a means for completely enclosing the target calculus in a container which prevents substantially all dissolution fluid from coming into contact with host tissue. In other words, a device is employed which has a containment means which produces an isolated local environment that includes the target calculus and does not allow dissolution fluid to contact the host tissue, even though the isolated local environment is produced in situ. Devices that find use in this embodiment of the subject invention further include a means for introducing dissolution fluid into and removing dissolution fluid from the isolated local environment produced by the device in situ.

Any convenient device that is capable of producing a flushable, isolated local environment around the target calculus in situ may be employed in this embodiment of the subject methods. One device that may be employed is the dissolution device of the subject invention, describe infra. Another device that may be employed is the device described in U.S. Pat. No. 5,275,605, the disclosure of which is herein incorporated by reference.

Additional Method Steps

In a number of embodiments of the subject methods, the above step of maintaining the local environment of the calculus at a subphysiological pH for a sufficient period of time for reduction in the mass of the target calculus to occur is used in conjunction with one or more additional method steps in order to achieve the overall mass reduction in the target calculus. Additional methods steps that may be present in the overall process include: (1) contacting with target calculus with one or more solutions in addition to the acidic dissolution solution; (2) applying external energy to the target calculus; and the like.

Additional Solutions

The subject methods may further include contacting the target calculus with one or more solutions in addition to the acidic dissolution solution. For example, where the exact nature of the target calculus is unknown, e.g. where the health care practitioner is unsure as to whether the target calculus is a calcium stone, a uric acid stone or a cystine stone, the target calculus may be contacted with a series of solutions, where one of the solutions is the acidic dissolution solution, and the other solutions may be designed to dissolve non-calcium containing calculi, e.g. tromethamine solution (THAM-E®), acetylcysteine solution (Mucomyst®), sodium bicarbonate solution, hemiacidrin solution (Renacidin®), Suby's solution G, the solutions disclosed in U.S. Pat. No. 4,845,125, the disclosure of which is herein incorporated by reference, and the like. Where a plurality of solutions are employed, the solutions are generally contacted with the target calculus sequentially. The number of different solutions contacted with the target calculus under this embodiment generally ranges from about 2 to 6, usually from about 2 to 4 and more usually from about 2 to 3.

Application of External Energy

In certain embodiments, external energy is applied to the target calculus to promote dissolution of the target calculus. Any means of applying external energy to the target calculus may be employed. As such, jets or other such means which are capable of providing varying external forces to the target calculus sufficient to cause the calculus to break up or disrupt may be employed. Of particular interest in many embodiments is the use of sonic energy, e.g., ultrasound. The ultrasound can be applied during the entire time of contact of the target calculus with the acidic treatment solution, the ultrasound can be applied for only part of the treatment period, or the ultrasound can be employed before or after the treatment with the acidic solution. There are several devices for the application of ultrasound to renal calculi known to those of skill in the art, where such devices include those described in U.S. Pat. Nos. 5,065,761; 5,065,741; 5,060,650; 4,984,575; 4,763,652 4,808,153, the disclosures of which are herein incorporated by reference.

Another means that may be employed to apply external energy to the target calculus during the dissolution process is to use a mechanical means of applying external energy. Mechanical means of interest include moving structures, e.g. rotating wires, which physically contact the target calculus and thereby apply physical external energy to the target calculus.

Reduction in Mass of the Target Calculus

Maintenance of the local environment of the target calculus at a subphysiologic pH, as described above, results in at least a reduction in the mass of the target calculus, e.g. a reduction of the calcium phosphate content of the target calculus which renders the target calculus lighter. By reduction is meant that the total overall dry weight of target calculus is reduced or decreased, generally by at least about 50%, usually by at least about 75% and more usually by at least about 80%. In certain embodiments, substantially all of the target calculus is dissolved, where by substantially all is meant at least about 90%, usually at least about 95% and preferably at least about 99% dry weight of the original target calculus is dissolved, such that less than 10%, usually less than 5% and more usually than 1% of the original mass of the target calculus remains following treatment.

Dissolution Devices

Also provided by the subject invention are novel dissolution devices for use in at least reducing the mass of the target calculus. The dissolution devices of the subject invention are characterized by having a means for enclosing a target renal calculus in a substantially isolated local environment in situ. This enclosing means is characterized by having an element that expands along a circumference about a central longitudinal axis to produce an isolated local environment. The isolated local environment produced upon expansion of the expansion means is characterized by having a circular cross-sectional shape in any plane normal to the longitudinal axis of the device. As such, upon full deployment of the expansion means, a substantially isolated local environment bounded by the walls of the deployed expansion means is produced. The devices of the subject invention are further characterized by having a least one fluid conduit which opens into the substantially isolated local environment produced upon full deployment of the expansion means of the device, where the at least one fluid conduit serves as an entryway and, in some embodiments exit, for the dissolution fluid.

For convenience, the subject novel dissolution devices are further described in terms of the figures. FIG. 1 provides a three-dimensional view of a dissolution device according to the subject invention. Device 10 includes portion 13, usually tubular, which houses one or more fluid conduits, represented as elements 14 and 16 in FIG. 1. Structure 13 may have a variety of different configurations, its sole purpose being to provide a housing for the fluid conduit(s) from their connection at the proximal end of the device to a fluid source to their outlet at the distal end of the structure. Generally, structure 13 is also configured such that the distal end can be positioned at the site of the target calculus. As such, structure 13 may be long rigid or flexible tube, depending on whether the distal end of the structure is introduced to the site of the target calculus by a body passageway, e.g. the ureter, or directly, e.g. via peripheral nepbrolithotomy procedures.

Figure 2:
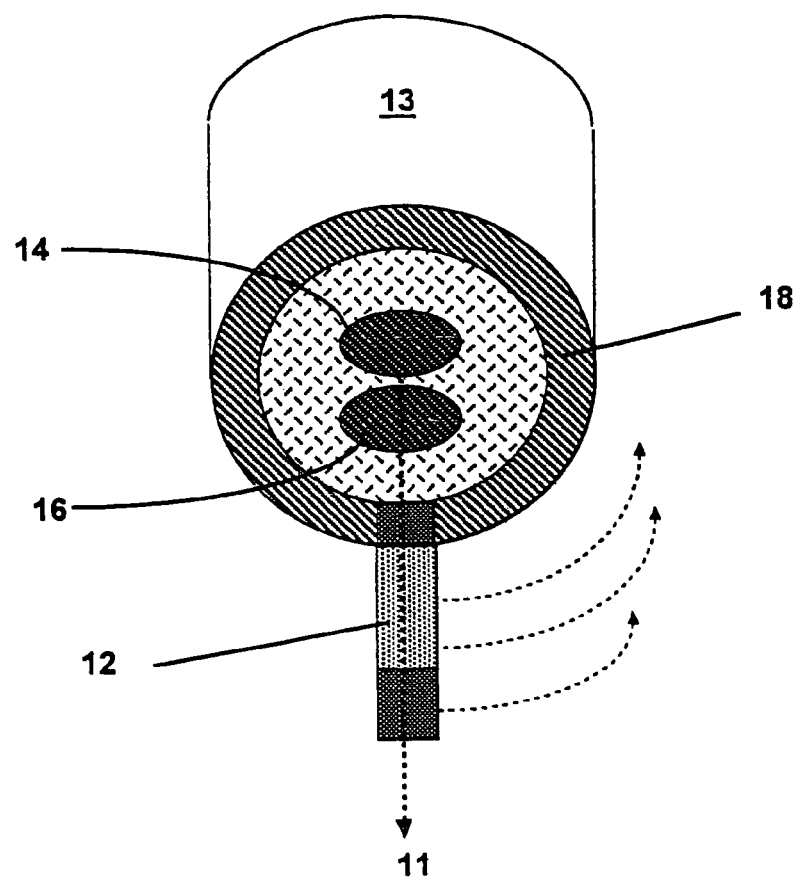
FIG. 2 provides a top, end-on view of the device shown in FIG. 1.

At the distal end of structure 13 is circumferential structure 18 to which is attached expansion means 12. Expansion means 12 has curvilinear profile in the embodiment shown in FIG. 1, but could also have a profile with another configuration, e.g. square, rectangular, triangular and the like. Longitudinal axis 11 of device 10 is shown as a dashed line with an arrow at one end. In deployment of the expansion means 12 to produce the isolated local environment, one side or edge of the expansion means 12 moves around a circumference of which longitudinal axis 11 is the central axis, as indicated by the curved dashed arrows. In other words, one side of expansion means 12 rotates about the longitudinal axis 11 to produce an enclosed, isolated local environment. FIG. 2 provides another perspective of the device shown in FIG. 1.

Figure 3:
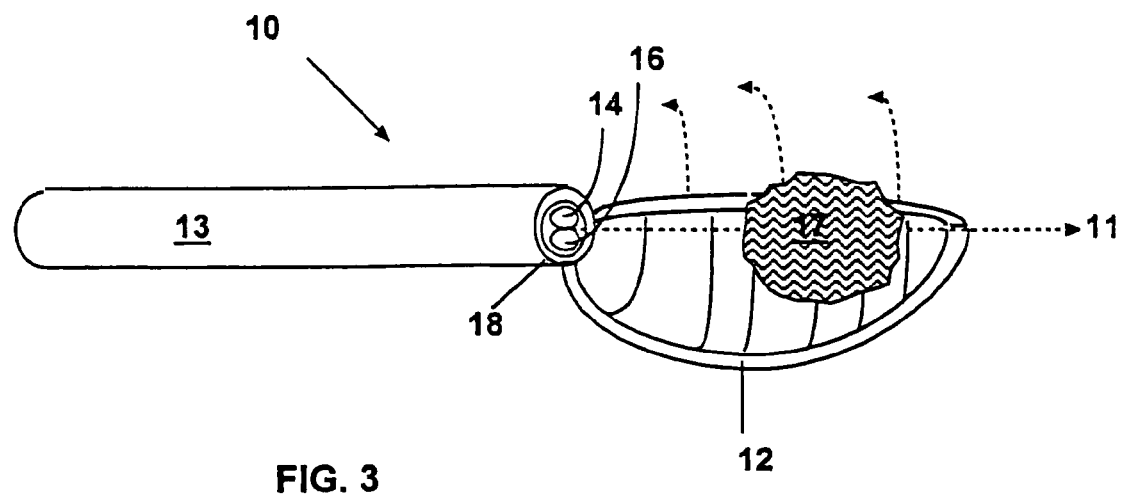
FIG. 3 provides a cross-sectional view of the device of FIG. 1 in which the isolated local environment formation means is partially deployed.
Figure 4:
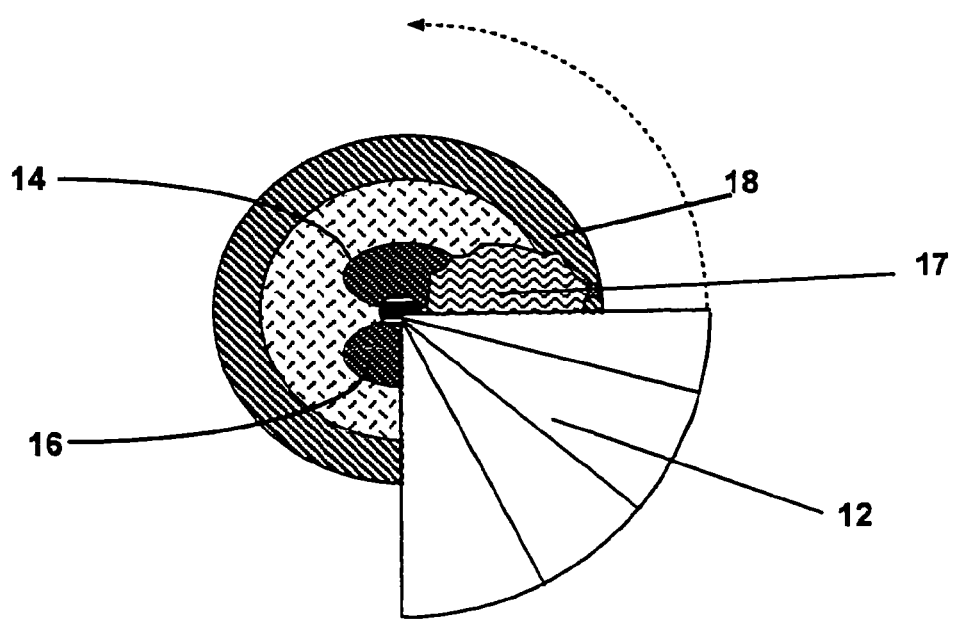
FIG. 4 provides an end on view of the partially deployed device of FIG. 3.

FIG. 3 shows the dissolution device in partial deployment around kidney stone 17. As can be seen in FIG. 3, expansion element 12 has been partially deployed in the direction of the curved arrows and is thereby enclosing an isolated local environment around the target kidney stone 17. An end on view of the device as shown in FIG. 3 is provided in FIG. 4.

Figure 5:
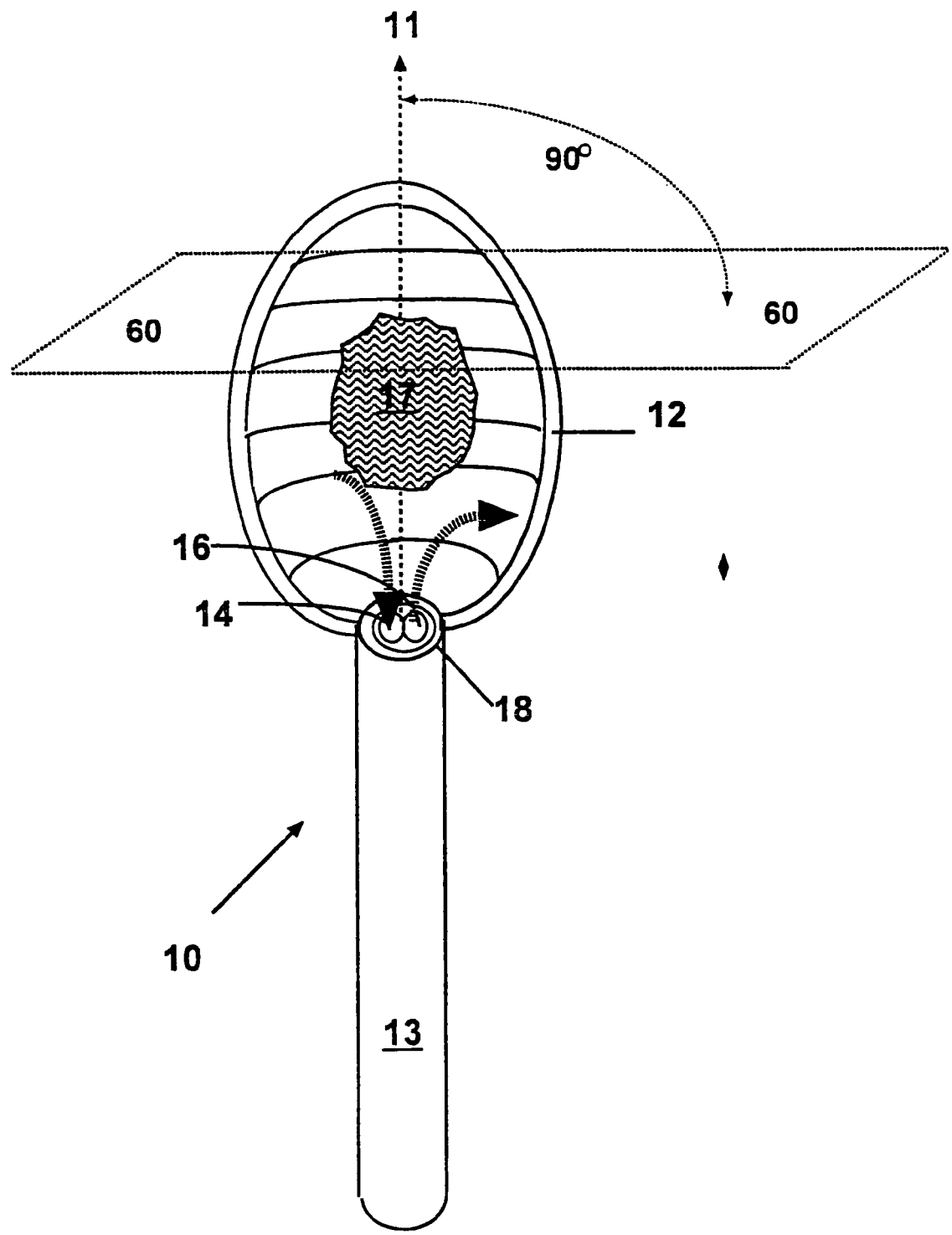
FIG. 5 provides a cutaway view of the device in FIG. 1 in which a kidney stone is enclosed in an isolated located environment bounded by a completely deployed element 12.

FIG. 5 provides a cutaway view of a completely deployed device in which target kidney stone 17 is completely enclosed in an isolated local environment bounded by the walls of the fully deployed expansion means 12. As shown in FIG. 5, once the target kidney stone is completely enclosed in an isolated local environment upon full deployment of expansion means 12, dissolution fluid is introduced through conduit 16 into the local environment and removed from the local environment by conduit 14, as indicated by the heavy dashed arrows. In this manner, the local environment and the target calculus present therein is flushed with the dissolution fluid in a manner such that the host tissue of the urinary tract in which the dissolution procedure is taking place is not contacted by the dissolution fluid.

Figure 6:
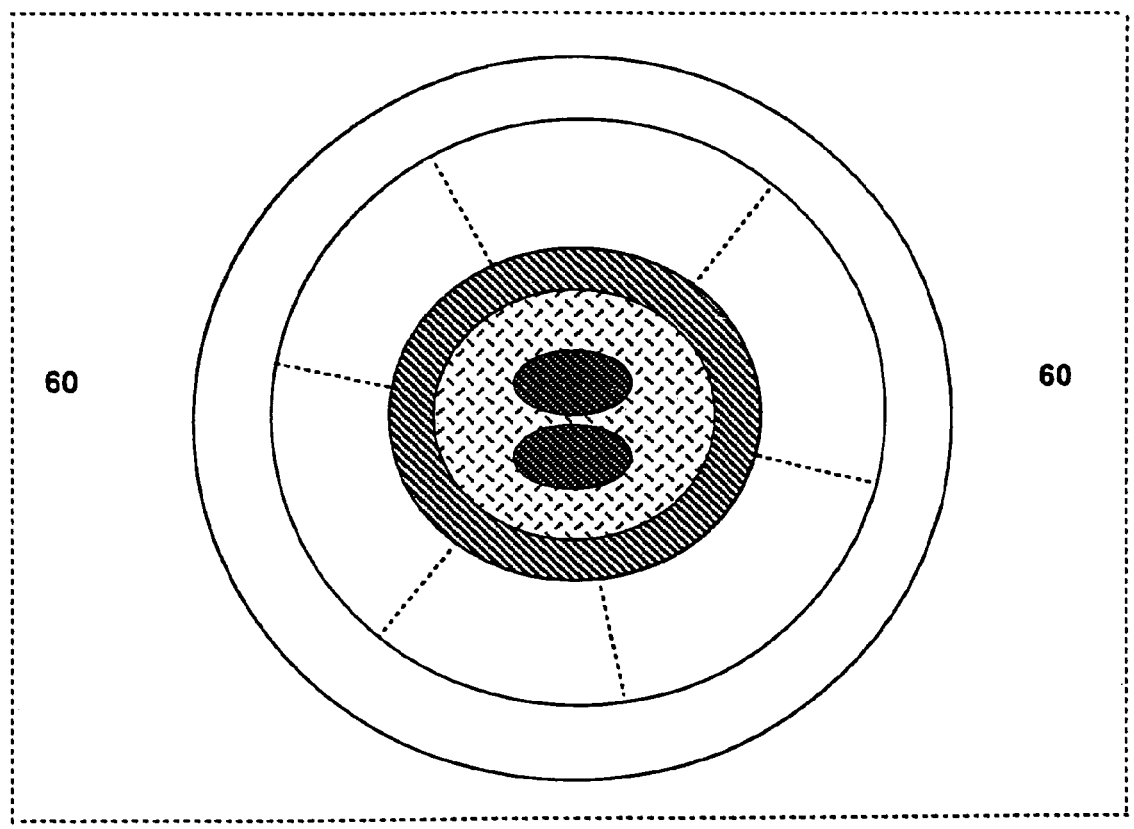
FIG. 6 provides a cross-sectional view of the device of FIG. 5 taken along plane 60, showing the circular cross-sectional profile produced upon full deployment of element 12.

FIG. 6 provides a cross-sectional view of the fully deployed expansion means 12 taken in plane 60 which is normal to the longitudinal axis 11 of the device 10. As shown in FIG. 6, the cross-sectional profile is circular, and this is true along the entire length of longitudinal axis 11, since the expansion means encloses the isolated local environment by expanding along a circumference in which the longitudinal axis 11 is the central axis, i.e. by having its leading edge rotate about the central longitudinal axis 11.

The dimensions of the dissolution device and elements thereof may vary, so long as the isolated local environment produced upon expansion of the expansion means is sufficient to enclosed the target calculus and the device can be introduced into the location of the target calculus.

The device may be fabricated from any convenient material which is capable of producing the device which meets the above parameters, e.g. allows for introducing of the device to the site of the target calculus (i.e. flexible in those embodiments where the device is introduced through narrow and/or tortuous access ways, e.g. the ureter); is physiologically compatible, at least during the treatment period; is capable of withstanding the solutions delivered by the device; etc. Fabricating a device according to the subject invention is well within the ability of those skilled in the art in view of the disclosure provided herein.

While the subject devices as depicted in FIGS. 1 to 6 are suitable for use in the methods of the subject invention in which an acidic dissolution solution of a strong, inorganic acid is employed, as described supra, the subject devices are also suitable for use with other chemolytic agents. Other chemolytic agents that find use in the dissolution of various types of renal calculi include: tromethamine solution (THAM-E®), acetylcysteine solution (Mucomyst®), sodium bicarbonate solution, hemiacidrin solution (Renacidin®), Suby's solution G, the solutions disclosed in U.S. Pat. No. 4,845,125, the disclosure of which is herein incorporated by reference, and the like.

Utility

The subject methods find use in a variety of different applications in which it is desired to at least reduce the mass of a renal calculus, including applications in which it is desired to completely dissolve a renal calculus. The subject methods find particular use in the treatment of disease conditions characterized by the presence of renal calculi, e.g. nephrolithiasis, also known as urolithiasis and urinary tract stone disease.

In treating such diseases according to the subject invention, treatment comprises at least reducing the mass of the renal calculi or kidney stones that are the underlying cause of the disease. As such, treatment also includes those embodiments in which the underlying kidney stones are completely dissolved by the subject methods. Treatment according to the present invention may also include the use of the subject methods in conjunction with one or more additional kidney stone treatment protocols, such as extracorporeal shockwave lithotripsy, percutaneous nephrolithotomy, and the like.

The subject methods and devices may be employed on a variety of hosts. Generally such hosts are "mammals" or "mammalian," where these terms are used broadly to describe organisms which are within the class Mammalia, including the orders carnivore (e.g., dogs and cats), Rodentia (e.g., mice, guinea pigs, and rats), Lagomorpha (e.g. rabbits) and primates (e.g., humans, chimpanzees, and monkeys). In many embodiments, the hosts will be humans.

Systems

Also provided by the subject invention are systems for use in performing the subject methods. The systems of the subject invention include at least a dissolution device, such as the subject devices described above, and a dissolution fluid reservoir capable holding or storing the dissolution fluid just prior to administration to the local environment of the target calculus. In addition, the subject systems will typically include a means for moving the dissolution fluid through the fluid introduction means to the local environment of the target calculus, where such means is typically a pump, large syringe, and the like. The system may also conveniently include a means for maintaining the pressure and/or temperature of the dissolution fluid at a desired value. In addition, the subject systems typically include a means for removing fluid from the local environment of the target calculus, e.g. a second pumping means or suction means. The above elements of the subject system may conveniently be present in housing fabricated of a suitable material.

Kits

Also provided are kits for use in performing the subject methods. The kits typically comprise at least the dissolution fluid to be used in the subject methods, such as a hydrochloric acid solution as described above, where the solution may be present in a storage means, such as a flexible bag or a rigid container. For kits that are to be used in methodologies in which the fluid is flushed through the local environment of the target calculus, the amount of dissolution fluid present in the kit ranges from about 1 to 500 liters, usually from about 10 to 200 liters and more usually from about 50 to 100 liters. For kits that are to be used in static methodologies, the amount of dissolution fluid present in the kit generally ranges from about 100 ml to 1 liter and usually from about 100 ml to 500 ml. Alternatively, the kit may comprise precursors of the dissolution solution for use in preparing the solution at the time of use. For example, the precursors may be provided in dry form for mixing with a fluid, e.g. water, at the time of use. Also present in the kit may be a dissolution device, as described supra. In addition to the dissolution fluid or precursors thereof, the kit may further comprise one or more additional fluids (or dry precursors thereof), such as solutions designed for the dissolution of non-calcium stones, such as those described supra. Finally, the kits will include instructions for practicing the subject methods, where such instructions may be present on one or more of the kit components, the kit packaging and/or a kit package insert.

The following examples are offered by way of illustration and not by way of limitation.

EXPERIMENTAL

I. Mineral Dissolution Assays

A. Norian SRS® cement (obtained from Norian Corporation, Cupertino, Calif.) is prepared according to the manufacturer's instructions. The resultant paste is placed into Teflon mold rings and allowed to set to produce dahllite disks. The disks are then contacted with the following solutions: 0.1 M HCl, 1.0 M HCl, concentrated HCl, 0.1 M HCl+0.01 M EDTA, 1.0 M HCl+0.01 M EDTA, concentrated HCl+0.1 M EDTA, 0.1 M $H_2SO_4$, 1.0 M $H_2SO_4$, 0.1 M $H_2SO_4$+0.01 M EDTA, 1.0 M $H_2SO_4$+0.1 M EDTA, 1.0 M formic acid, concentrated formic acid, 1.0 M formic acid+0.1 M EDTA, 1.0 M acetic acid, concentrated acetic acid, 1.0 M acetic acid and 0.1 M EDTA, 1.0 M succinic acid, 1.0 M succinic acid+0.1 M EDTA; 0.1 M carbonic acid; and 1.0 M carbonic acid. A dissolution graph is then prepared for each solution which plots $Ca^{2+}$ concentration over time. By comparing the different dissolution graphs, the solubility of dahllite in different dissolution solutions is compared.

B. Dissolution of Bolus of Dahllite in 0.05 N HCl with Various Ionic Strengths Using Pump at 69 ml/min 1. Introduction Six dissolution experiments were conducted to determine the affect of ionic strength on the dissolution rate of carbonated hydroxyapatite in HCl. According to the Kinetic Salt Effect theory, oppositely charged ions react more slowly as the ionic strength of the solution is increased because the electrostatic attraction between the reacting ions is decreased. The object of this experiment was to determine if the theory holds for the dissolution reaction of carbonated hydroxyapatite with HCl.

2. Experimental

A Cole-Parmer peristaltic pump (model #7520-35) was used to deliver the demineralizing 0.05N HCl solution with varying NaCl concentrations to the sample of carbonated hydroxyapatite (i.e. dahllite), $Ca_{8.8}(HPO_4)_{0.7}(PO_4)_{4.5}$ $(CO_3)_{0.7}(OH)_{1.3}$, in the form of a spherical bolus. In each case, a 100±3 mg bolus (dry weight) of carbonated hydroxyapatite was soaked in deionized water until there was no further weight gain. This weight was taken to be the initial weight of the bolus. The bolus was then transferred to a 12 ml disposable liquid transfer pipette and a peristaltic pump with a rubber stopper on one end of the tubing was attached. Solutions were pumped through the pipette past the bolus at a rate of approximately 69 ml/min in 5 minute time intervals and the weight of the bolus was measured at the end of each interval. The dissolution process was continued until the weight of the bolus was less than 5 mg. The NaCl concentrations used were: 0, 5.8 (isotonic), 11.6, and 25 g/L.

3. Results

The results of the six dissolution experiments are tabulated below. A table of the respective half-lives follows. The wet weight of the bolus at t=0 is represented by m(o), and m(t) is the weight at a given time interval (m=mass).

TABLE 1

Dissolution of Bolus of 0.05N HCl with Various Ionic Strengths

| | | | log[m(t)/m(0)] | | | |
|---|---|---|---|---|---|---|
| | No salt | No salt (2) | 5.8 g NaCl | 5.8 g NaCl (2) | 11.6 g NaCl | 25 g NaCl |
| Time (min) | | | | | | |
| 0.0 | 0.0000 | 0.0000 | 0.0000 | 0.0000 | 0.0000 | 0.0000 |
| 5.0 | −0.0569 | −0.0982 | −0.0789 | −0.0822 | −0.1209 | −0.1300 |
| 10.0 | −0.1374 | −0.2121 | −0.1926 | −0.1803 | −0.2287 | −0.3014 |
| 15.0 | −0.2403 | −0.3212 | −0.3322 | −0.2906 | −0.3973 | −0.5792 |
| 20.0 | −0.3594 | −0.4491 | −0.5195 | −0.4514 | −0.6717 | |
| 25.0 | −0.4765 | −0.5907 | −0.8683 | −0.6736 | | |
| 30.0 | −0.6273 | −0.7788 | | −1.2653 | | |
| 35.0 | −0.8154 | −1.0740 | | | | |
| Half-lives for the Dissolution of Bolus in 0.05N HCl | | | | | | |
| Half-life (min) | 15.8 | 12.7 | 11.6 | 11.8 | 10.5 | 8.8 |

4. Discussion and Conclusion

The half-life data and log [m(t)/m(0)] vs. time show that increasing the ionic strength of the solution increases the dissolution rate. This contradicts the Kinetic Salt Effect theory which says that increasing the ionic strength of a solution decreases the reaction rate between oppositely charged ions due to a decrease in electrostatic attraction between the ions. In this case, $Na^+$ and $Cl^-$ ions should theoretically decrease the electrostatic attraction between $H^+$ and both $HPO_4^{2-}$ and $PO_4^{3-}$ and slow the rate of dissolution.

C. Dissolution of Bolus in HCl Solutions of Various pH

1. Introduction

Eight sets of dissolution experiments were conducted to determine the affect of pH on the dissolution rate of carbonated hydroxyapatite in HCl. It was predicted that a decrease in pH (increase in $H^+$) should increase the rate of dissolution. In addition, three different methods of dissolution were used to see how altering the method would affect the dissolution rate.

2. Experimental

For each experiment, a 100±3 mg (dry weight) sample of carbonated hydroxyapatite, $Ca_{8.8}(HPO_4)_{0.7}(PO_4)_{4.5}(CO_3)_{0.7}(OH)_{1.3}$, in the form of a spherical bolus was used. The bolus was soaked in deionized water until there was no further weight gain and this weight was taken to be the initial weight of the bolus. Descriptions of the three dissolution methods are below. For each set of experiments, nine pH levels were studied.

i. Stirring

For the stirring experiments, the bolus was placed in a beaker with a volume of HCl solution that provided twice the stoichiometric number of protons necessary to dissolve the carbonated hydroxyapatite. A stir bar of appropriate size was added to the beaker and the solution was stirred on an IKA Labortechnik stir plate on a setting of 6. For each experiment, the weight of the bolus was measured at time intervals appropriate for the pH of the solution used until the weight of the bolus was less than 5 mg. pK was calculated from the slope of the linear regression line for each set of data points using the following formula:

$$pK = -\log [1.533 * slope]$$

ii. Sonication

Sonication experiments employed a Branson Sonifier 450 to deliver ultrasound to the HCl solution. Power outputs of 9 Watts, 35 Watts, and 53 Watts were used. The solutions were also stirred on an IKA Colorsquid stir plate on a setting of 2 to ensure complete mixing. The bolus was placed in a beaker with a volume of HCl solution that provided twice the stoichiometric number of protons necessary to dissolve the it, and weight measurements were made at time intervals appropriate for the pH of the solution until the weight was less than 5 mg. pK was calculated as it was for the stirring experiments.

iii. Pump

A Cole-Parmer peristaltic pump (model #7520-35) was used to deliver the HCl solution to bolus. The bolus was placed in a 12 ml disposable liquid transfer pipette and the peristaltic pump with a rubber stopper on one end of the tubing was attached. Solutions were pumped through the pipette past the bolus at rates of approximately 16 ml/min, 33 ml/min, 69 ml/min, and 110 ml/min. Weight measurements were made at appropriate time intervals until the weight was less than 5 mg, and pK was calculated as before.

3. Results

The results of the eight sets of dissolution experiments are included in Table 2 below. Graphs were also generated from the observed data. Rate measurements for 0.8N, 0.6N and 0.075N were not taken for the sonication and pump experiments because the slope of the pK vs. pH linear regression line for the stirring experiment was relatively unchanged by including these points. Note that a lower pK indicates a faster dissolution rate.

TABLE 2 pKs Resulting from Dissolution of Bolus with Various HCl Solutions and Various Dissolution Methods

| HCl concentration (N) | pH | Stirring | Sonication 9 W | Sonication 35 W | Sonication 53 W | Pump 16 ml/min | Pump 33 ml/min | Pump 69 ml/min | Pump 110 ml/min |
|---|---|---|---|---|---|---|---|---|---|
| 1.000 | 0.000 | 0.7189 | 0.1997 | 0.2634 | 0.3557 | 0.4190 | 0.2710 | 0.2392 | 0.2069 |
| 0.800 | 0.097 | 0.8204 | | | | | | | |

TABLE 2-continued pKs Resulting from Dissolution of Bolus with Various HCl Solutions and Various Dissolution Methods

| HCl concentration (N) | pH | Stirring | Sonication 9 W | Sonication 35 W | Sonication 53 W | Pump 16 ml/min | Pump 33 ml/min | Pump 69 ml/min | Pump 110 ml/min |
|---|---|---|---|---|---|---|---|---|---|
| 0.600 | 0.222 | 1.1122 | | | | | | | |
| 0.400 | 0.398 | 1.2840 | 0.7086 | 0.5689 | 0.6252 | 0.8400 | 0.5717 | 0.4875 | 0.4195 |
| 0.200 | 0.699 | 1.6950 | 0.9987 | 0.8799 | 0.6922 | 1.1140 | 0.9887 | 0.7103 | 0.7015 |
| 0.100 | 1.000 | 1.8600 | 1.4970 | 1.1693 | 1.1146 | 1.2390 | 1.1524 | 1.0674 | 0.8288 |
| 0.075 | 1.125 | 2.0310 | | | | | | | |
| 0.050 | 1.301 | 1.9440 | 1.9612 | 1.4658 | 1.5364 | 1.5020 | 1.4340 | 1.2938 | 0.9704 |
| 0.001 | 2.000 | 2.2440 | 2.3607 | 2.3773 | 2.0659 | 2.3240 | 1.9982 | 1.8080 | 1.6649 |

4. Discussion and Conclusion

Several conclusions may be drawn from the results of these experiments. First, the positive slopes of the lines on the pK vs. pH graph (not shown) show that a decrease in pH of the solution (increase in $H^+$) results in an increase in dissolution rate (decrease in pK) as expected. The dissolution involves $H^+$, $HPO_4^{2-}$ and $PO_4^{2-}$ ions, so it makes sense that increasing $H^+$ should increase the dissolution rate.

Both sonication and the pump gave faster dissolution rates than stirring alone. This is most likely due to the fact that sonication and pumping provide better mixing of the solution, effectively removing any layer of dissolved or reprecipitated material from the immediate area surrounding the bolus.

For the sonication experiments, increasing the ultrasonic power increased the rate of dissolution. When ultrasound was used, tiny craters in the surface of the bolus were observed. Increasing the ultrasonic power may help dissolution by either increasing the surface area due to these craters, increasing the mixing of the solution, or both. It may also dislodge particles from the surface of the bolus that are not yet dissolved.

Of the three dissolution methods studied, the pump gave the fastest dissolution rate. The rate consistently increased as the pump flow rate was increased. The maximum flow rate for the peristaltic pump that was used was 110 ml/min, but it is anticipated that a faster dissolution rate may be achieved by using a faster pump. The faster rate may be attributed to the fact that a larger volume of solution (more than double the stoichiometric number of protons) must be used with the pump, and that the bolus is always exposed to fresh solution which is equivalent to ultimate mixing. The stream of solution may also mechanically remove particles from the bolus.

One final observation from the pK vs. pH graph is that differences in rate for the different methods decrease as pH decreases. In other words, rates vary less at pH 0 and vary more at pH 2. Therefore, for solutions of higher proton concentration, the rate of dissolution is less dependent on the method employed.

D. Dissolution of Bolus in HCl Solutions using Ultrasound

1. Introduction.

Six sets of dissolution experiments were conducted to determine the effect of Ultrasound on the dissolution rate of carbonated hydroxyapatite in HCl. It was predicted that an increase in ultrasonic power should increase the rate of dissolution due to an increase in mixing of the solution.

2. Experimental For each experiment, a 100±3 mg (dry weight) sample of carbonated hydroxyapatite, $Ca_{8.8}(HPO_4)_{0.7}(PO_4)_{4.5}(CO_3)_{0.7}(OH)_{1.3}$, in the form of a spherical bolus was used. The bolus was soaked in deionized water until there was no further weight gain and this weight was taken to be the initial weight of the bolus. The bolus was placed in a beaker with a volume of HCl solution that provided twice the stoichiometric number of protons necessary to dissolve it, and a Branson Sonifier 450 was employed to deliver ultrasound to the solution. Various HCl solutions were employed. The 0.1N, 0.05N, and 0.01N HCl solutions were made isotonic (300 mOsmol) with NaCl. Power outputs of 9 Watts, 35 Watts, and 53 Watts were used. The solutions were also stirred on an IKA Colorsquid stir plate on a setting of 2 to ensure complete mixing. Weight measurements were made at time intervals appropriate for the pH of the solution until the weight was less than 5 mg. pK was calculated from the slope of the linear regression line for each set of data points using the following formula:

$$pK = -\log[1.533 * slope]$$

3. Results

The results of the six sets of dissolution experiments are tabulated below in Table 3. Note that a lower pK indicates a faster dissolution rate.

TABLE 3

| Ultrasonic Power (Watts) | 1N HCl | 0.4N HCl | 0.2N HCl | 0.1N HCl | 0.05N HCl | 0.01N HCl |
|---|---|---|---|---|---|---|
| pKs Resulting from Dissolution of Bolus Using Ultrasound | | | | | | |
| 9 | 0.1997 | 0.7086 | 0.9987 | 1.497 | 1.9612 | 2.3607 |
| 35 | 0.2634 | 0.5689 | 0.8799 | 1.1693 | 1.4658 | 2.3773 |
| 53 | 0.3557 | 0.6252 | 0.6922 | 1.1146 | 1.5364 | 2.0659 |
| Half-lives (in min) Resulting from Dissolution of Bolus Using Ultrasound | | | | | | |
| 9 | 1.1 | 3.6 | 6.8 | 18.5 | 48.3 | 130.5 |
| 35 | 1.2 | 2.2 | 4.3 | 8.9 | 15.6 | 130.7 |
| 53 | 1.2 | 2.6 | 3 | 7.9 | 19.3 | 64.2 |

4. Discussion and Conclusion

The half-life data table shows that when the ultrasonic power was increased from 9 Watts to 35 Watts, the rate of dissolution increased for all solutions except 1N HCl and 0.01N HCl for which the rates remained relatively unchanged. The 1N HCl solution dissolves the bolus so quickly that any minor rate changes are difficult to observe. It is unclear why there was no observable increase in dissolution rate for the 0.01N solution. When the ultrasonic power was increased to 53 Watts, dissolution rates increased for all solutions except 1N and 0.4N, for which rates remained relatively unchanged, and 0.05N for which the rate decreased slightly. The results indicate that increasing the ultrasonic power increased the dissolution rate except when the rate is already so fast that minor changes are difficult to observe.

E. Dissolution of Bolus in HCl Solutions Using Pump

1. Introduction.

Six sets of dissolution experiments were conducted to determine the effect of pump flow rate on the dissolution rate of carbonated hydroxyapatite in HCl. It was predicted that an increase in flow rate should increase the rate of dissolution due to an increase in exposure to protons.

2. Experimental.

For each experiment, a 100±3 mg (dry weight) sample of carbonated hydroxyapatite, $Ca_{8.8}(HPO_4)_{0.7}(PO_4)_{4.5}(CO_3)_{0.7}(OH)_{1.3}$, in the form of a spherical bolus was used. The bolus was soaked in deionized water until there was no further weight gain and this weight was taken to be the initial weight of the bolus. The bolus was placed in a 12 ml disposable liquid transfer pipette and a Cole-Parmer peristaltic pump (model #7520-35) with a rubber stopper on one end of the tubing was attached. Various HCl solutions were pumped through the pipette past the bolus at rates of approximately 16 ml/min, 33 ml/min, 69 ml/min, and 110 ml/min. The 0.1N, 0.05N, and 0.01N HCl solutions were made isotonic (300 mOsmol) with NaCl. Weight measurements were made at, time intervals appropriate for the pH of the solution until the weight was less than 5 mg. pK was calculated from the slope of the linear regression line for each set of data points using the following formula:

$$pK = -\log[1.533 * slope]$$

3. Results.

The results of the six sets of dissolution experiments are tabulated below. Note that a lower pK indicates a faster dissolution rate.

TABLE 4

| Pump Flow Rate (ml/min) | 1N HCl | 0.4N HCl | 0.2N HCl | 0.1N HCl | 0.05N HCl | 0.01N HCl |
|---|---|---|---|---|---|---|
| pKs Resulting from Dissolution of Bolus Using Pump | | | | | | |
| 16 | 0.4190 | 0.8400 | 1.1140 | 1.2390 | 1.5020 | 2.3240 |
| 33 | 0.2710 | 0.5717 | 0.9887 | 1.1524 | 1.4340 | 1.9982 |
| 69 | 0.2392 | 0.4850 | 0.7103 | 1.0674 | 1.2938 | 1.8084 |
| 110 | 0.2069 | 0.4195 | 0.7015 | 0.8288 | 0.9704 | 1.6649 |
| Half-lives (in min) Resulting from Dissolution of Bolus Using Pump | | | | | | |
| 16 | 1.5 | 3.9 | 7.6 | 10.0 | 21.1 | 110.5 |
| 33 | 1.1 | 2.2 | 5.5 | 9.2 | 15.3 | 61.5 |
| 69 | 1.0 | 1.5 | 3.0 | 6.7 | 11.6 | 38.8 |
| 110 | 0.8 | 1.6 | 2.8 | 4.8 | 6.4 | 29.2 |

4. Discussion and Conclusion

The data show an obvious increase in dissolution rate as the pump speed is increased. 110 ml/min was the fastest flow rate that could be attained with this pump, however it is likely that the dissolution rate would continue to increase with a faster pump. The increase in rate may be attributed to the increase in exposure of the bolus to protons. Mechanical removal of surface particles may also play a role.

II. Formulations (A) Solution A=1.0 N HCl+0.25 M NaCl.
(B) Solution B=0.5 N HCl+0.25M NaCl.
(C) Solution C=0.1 N HCl+0.05 M NaCl.
(D) A suitable formulation for acidic treatment under a constant flow rate comprises:

| | |
|---|---|
| Formic acid (concentrated) | 10% |
| Sodium dodecyl sulfate (SDS) | 0.1% |
| $H_2O$ | qs 100% |

(E) An alternative formulation for acidic treatment under a constant flow rate comprises:

| | |
|---|---|
| HCl (concentrated) | 10% |
| EDTA | 0.1% |
| $H_2O$ | qs 100% |

(F) An alternative formulation for acidic treatment under a constant flow rate comprises:

| | |
|---|---|
| Phosphoric acid (concentrated) | 10% |
| $H_2O$ | qs 100% |

(G) An alternative formulation for acidic treatment under a constant flow rate comprises:

| | |
|---|---|
| Sulfuric acid (concentrated) | 10% |
| $H_2O$ | qs 100% |

(H) An alternative formulation for acidic treatment under a slower rate or under static conditions comprises:

| | |
|---|---|
| Tris HCl | 0.1 M | pH adjusted to 4.2 with concentrated HCl.

It is evident from the above results and discussion that the above invention provides a simple, rapid and effective means for at least reducing the mass of, if not completely dissolving, renal calculi, particularly calcium renal calculi, in situ. As such, the subject invention provides an important new means for treating disease conditions associated with the presence of renal calculi, such as nephrolithiasis and related conditions. Accordingly, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for at least reducing the mass of a calcium comprising renal calculus, said method comprising:

introducing an elongated device into an organ of a living organism, the elongated device having at least one lumen extending therethrough;

creating an isolated local environment at the end of the elongated device and around the renal calculus by rotating an expansion device that extends from the elongated device about the longitudinal axis of the elongated device to encapsulate the renal calculus therein, wherein rotating the expansion device creates the isolated local environment by expansion of the expansion device, the expansion device comprises a single curvilinear element that initially does not create a volume for the renal calculus and then expands, via rotation, along a circumference about a central longitudinal axis to produce said isolated local environment which is characterized by having a circular cross-sectional shape in any plane normal to said longitudinal axis to create a volume for enclosing the renal calculus;

enclosing the renal calculus in the expansion device in a manner such that the renal calculus is positioned within an isolated local environment in situ and in fluid communication with the at least one lumen; and flushing said isolated local environment with a continuous flow of hydrochloric acid dissolution solution for a period of time of ranging from about 5 to 30 minutes by introducing and removing said solution from said isolated local environment at substantially the same rate and maintaining a substantially constant pressure in said isolated local environment, said hydrochloric acid dissolution solution being hypertonic with an osmolarity of greater than 300 mosmol and having a pH of 1 or less, and the total amount of fluid passing through the isolated local environment is from about 0.5 to 2.0 liters;

wherein the dissolution fluid is removed at substantially the same rate as it is introduced such that the volume of solution and the pressure in the isolated local environment remains substantially constant, thereby minimizing traumatic impact on vessel walls of the isolated local environment.

* * * * *